United States Patent
Becker et al.

(10) Patent No.: US 8,316,462 B2
(45) Date of Patent: *Nov. 27, 2012

(54) TIP-TO-WORK DISTANCE COMMUNICATION SYSTEM FOR A WELDING MASK

(75) Inventors: William Joshua Becker, Manitowoc, WI (US); Kyle Andrew Pfeifer, Appleton, WI (US)

(73) Assignee: Illinois Tool Works Inc., Glenview, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/165,257

(22) Filed: Jun. 21, 2011

(65) Prior Publication Data

US 2011/0248864 A1   Oct. 13, 2011

Related U.S. Application Data

(63) Continuation of application No. 12/425,252, filed on Apr. 16, 2009, now Pat. No. 7,962,967.

(51) Int. Cl.
*A61F 9/06* (2006.01)
*A61F 9/04* (2006.01)

(52) U.S. Cl. .............. 2/8.1; 2/8.2; 2/8.3; 2/8.5; 2/8.8

(58) Field of Classification Search .......... 2/410, 6.1, 2/6.3, 6.6, 6.7, 7, 8.1–8.8, 417–422; 218/130.01, 218/147

See application file for complete search history.

(56) References Cited

U.S. PATENT DOCUMENTS

| | | | | |
|---|---|---|---|---|
| 2,045,800 A | * | 6/1936 | Richter | 315/135 |
| 2,045,802 A | * | 6/1936 | Richter | 340/815.73 |
| 2,351,910 A | * | 6/1944 | Blankenbuehler | 340/660 |
| 4,124,944 A | | 11/1978 | Blair | |
| 4,237,557 A | * | 12/1980 | Gordon | 2/8.8 |
| 4,555,614 A | * | 11/1985 | Morris et al. | 219/130.01 |
| 4,677,277 A | * | 6/1987 | Cook et al. | 219/130.01 |
| 4,716,273 A | * | 12/1987 | Paton et al. | 219/130.1 |
| 4,721,947 A | * | 1/1988 | Brown | 340/540 |
| 5,317,643 A | * | 5/1994 | Patricelli | 381/376 |
| 5,708,460 A | * | 1/1998 | Young et al. | 345/173 |
| 5,845,053 A | | 12/1998 | Watanabe et al. | |
| 6,242,711 B1 | * | 6/2001 | Cooper | 219/130.01 |
| 6,614,409 B1 | * | 9/2003 | Bae | 345/8 |
| 6,710,298 B2 | * | 3/2004 | Eriksson | 219/130.01 |
| 7,150,047 B2 | * | 12/2006 | Fergason | 2/8.1 |

(Continued)

FOREIGN PATENT DOCUMENTS

EP   0963744 A1   12/1999

OTHER PUBLICATIONS

International Search Report and Written Opinion for application No. PCT/US2009/042658 mailed Aug. 25, 2009.

*Primary Examiner* — Bobby Muromoto, Jr.
(74) *Attorney, Agent, or Firm* — Fletcher Yoder P.C.

(57) ABSTRACT

A system enables transmitting a torch angle and/or a torch-to-workpiece distance error to a welding operator when these parameters are outside of a preset optimal range via real time audio cues. Weld characteristics are communicated via audio signals, which indicate to the welding operator the direction and severity of the torch angle error. Audio cues, such as pulsed or continuous tones, are used to communicate torch-to-workpiece distance to the welding operator.

20 Claims, 9 Drawing Sheets

U.S. PATENT DOCUMENTS

| | | | |
|---|---|---|---|
| 7,161,135 B2 * | 1/2007 | Fergason | 250/221 |
| 7,209,039 B2 * | 4/2007 | Krebs | 340/572.1 |
| 7,212,300 B2 * | 5/2007 | Comer et al. | 358/1.15 |
| 7,265,746 B2 * | 9/2007 | Knowles et al. | 345/173 |
| 7,298,535 B2 * | 11/2007 | Kuutti | 359/16 |
| 7,342,210 B2 * | 3/2008 | Fergason | 250/206 |
| 7,383,654 B2 * | 6/2008 | Olivier et al. | 40/661.12 |
| 7,411,154 B2 * | 8/2008 | Fosbinder et al. | 219/130.1 |
| 7,501,613 B2 * | 3/2009 | Fergason | 250/216 |
| 7,534,005 B1 * | 5/2009 | Buckman | 362/105 |
| 7,550,698 B2 * | 6/2009 | Fergason | 250/201.1 |
| 7,683,290 B2 * | 3/2010 | Daniel et al. | 219/130.01 |
| 7,962,967 B2 * | 6/2011 | Becker et al. | 2/8.1 |
| 2002/0124271 A1 * | 9/2002 | Herrmann et al. | 725/151 |
| 2003/0083112 A1 * | 5/2003 | Fukuda | 455/568 |
| 2007/0086508 A1 * | 4/2007 | Reading et al. | 374/208 |
| 2008/0158502 A1 * | 7/2008 | Becker et al. | 351/44 |
| 2008/0169277 A1 * | 7/2008 | Achtner et al. | 219/136 |
| 2009/0094721 A1 * | 4/2009 | Becker | 2/8.8 |
| 2009/0231423 A1 * | 9/2009 | Becker et al. | 348/82 |
| 2009/0276930 A1 * | 11/2009 | Becker et al. | 2/8.2 |

* cited by examiner

TIP-TO-WORK DISTANCE COMMUNICATION SYSTEM FOR A WELDING MASK

CROSS REFERENCE TO RELATED APPLICATIONS

This application is a continuation of U.S. application Ser. No. 12/425,252, filed Apr. 16, 2009, entitled "Weld Characteristic Communication System for a Welding Mask" in the name of William Joshua Becker et al., which claims priority to Provisional Application No. 61/143,261, filed Jan. 8, 2009, and Provisional Application No. 61/051,954, filed May 9, 2008.

BACKGROUND

Embodiments of the present disclosure relate generally to weld communication systems, and more particularly, to systems and methods for intuitively communicating weld characteristics to a welding operator in real time.

Welding is a process that has increasingly become ubiquitous in all industries. While such processes may be automated in certain contexts, a large number of applications continue to exist for manual welding operations, the success of which relies heavily on the proper use of a welding gun or torch by a welding operator. For instance, an improper torch angle can lead to spatter, improper penetration, and overall poor weldments. However, inexperienced welding operators often have difficulty establishing the proper torch angle and torch-to-workpiece distance during welding, and such parameters may be somewhat difficult to estimate during the process of making a weld. Furthermore, even experienced welding operators may have difficulty monitoring and maintaining these important parameters throughout welding processes.

Traditionally, welding operators rely on the sound and look of the weld to approximate the proper torch angle and torch-to-workpiece distance based on experience. It is now recognized that such traditional methods may lead to excess consumable waste, especially during training exercises.

BRIEF DESCRIPTION

The present disclosure is directed to systems and methods relating to a real time weld characteristic communication in an intuitive fashion. In particular, the present disclosure provides methods and systems for transmitting a torch angle and a torch-to-workpiece distance error to a welding operator in real time when these parameters are outside of a preset optimal range via intuitive visual and audio cues. One embodiment of the present disclosure relates to weld characteristic communication via intuitive arrays of visual indicators located on the periphery of a lens, which indicate to the welding operator the direction and severity of the torch angle error. In one embodiment, audio cues, such as pulsed or continuous tones may be used to communicate torch-to-workpiece distance to the welding operator. In certain embodiments, vertical visual indicator arrays may be used to indicate additional weld or auxiliary information, such as battery charge state, torch speed and so forth, to the welding operator. In one embodiment, all the components of the communication system may be located in or on a welding helmet and/or welding goggles. In other embodiments, some of the components of the communication system may be located in a belt pack.

DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Apparatuses have been proposed that are used to monitor weld characteristics and provide feedback to the welding operator during welding. However, these traditional devices are generally not intuitive. For example, such devices generally require substantial knowledge of device programming and often require a welding operator to make indirect associations in order to interpret provided information such that proper adjustments can be made. Indeed, these traditional devices typically provide welding operators with an overload of difficult to decipher information. Thus, it is now recognized that there exists a needs for a device that will communicate in an intuitive fashion to a welding operator whether the torch angle and/or torch-to-workpiece distance during a weld falls within an optimal range. Accordingly, present embodiments are directed to systems and methods relating to real time weld characteristic communication in an intuitive fashion.

Figure 1:
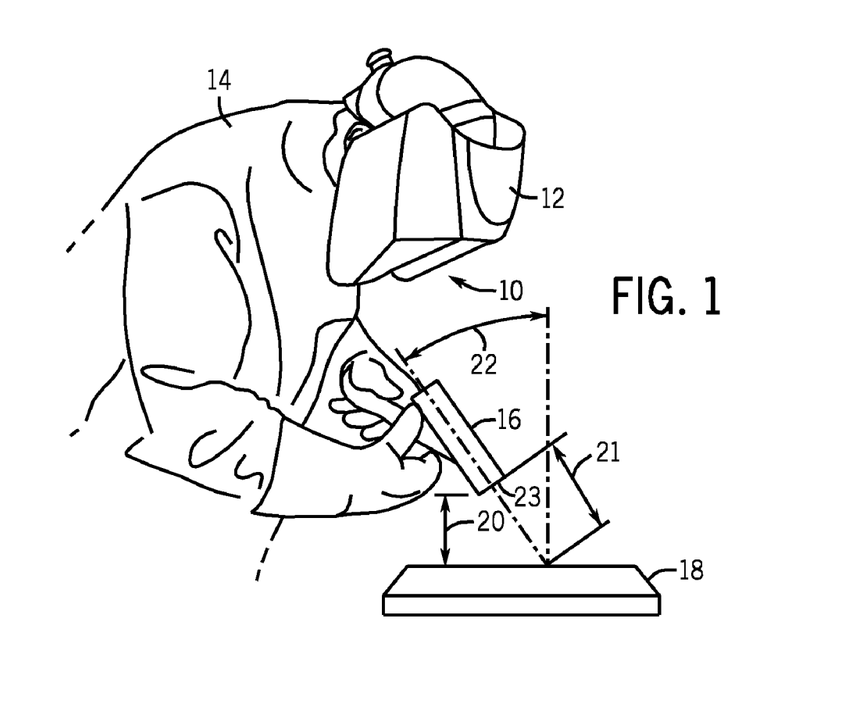
FIG. 1 illustrates an exemplary weld communication system positioned in or on a welding helmet worn by a welding operator during a weld in accordance with aspects of the present disclosure.

FIG. 1 illustrates a weld communication system 10 positioned in or on a welding helmet 12 worn by a welding operator 14. A welding operation will typically be powered and controlled by a welding system, which interfaces with a welding torch 16. During the welding operation, the welding torch 16 may be manipulated by the welding operator 14 to form an arc between the torch 16 and a workpiece 18 to initiate a weld process. During the welding operation, a position of the torch 16 may be defined by a tip-to-work distance 20 and a torch angle 22. The tip-to-work distance 20 may include the vertical distance from a tip 23 of the torch 16 to the workpiece 18 as illustrated in FIG. 1. In other embodiments, the tip-to-work distance 21 may be the distance from the tip 23 of the torch 16 to the workpiece 18 in the direction of the torch 16 (i.e. the distance from the tip 23 of the torch 16 at the angle of the torch 16 to the workpiece 18). The torch angle 22 may include an indication of the angular position of the torch 16 relative to the workpiece 18 and may be measured in one axis or two axes. In other embodiments, additional sensors may be used to track the location and/or angle of the welding mask. The feedback information from these sensors could be combined with the torch angle vector to ensure that the angle indicator LEDs are always illuminated properly with respect to the welding operator's angular perspective of the weldment.

The communication system 10 simultaneously communicates one or more welding characteristics in substantially real time to the welding operator 14. Additionally, the communication system 10 informs the welding operator 14 which action should be undertaken to correct any deviations from preset ranges. For instance, the communication system 10 may use visual cues to show the welding operator 14 the direction of torch angle 22 error and audio and/or visual cues to indicate tip-to-work distance 20 error during the weld. The welding operator 14 may then correct the torch angle 22 and tip-to-work distance 20 to achieve a proper weld. In the illustrated embodiment, the communication system 10, which includes both visual and audio systems incorporated into the welding helmet 12, is configured to inform the welding operator 14 of weld characteristics, such as the tip-to-work distance 20, the torch angle 22, torch travel speed, weld number and so forth, in substantially real time. The communication system 10 may utilize audio, visual, and/or audio-visual indicators and messaging techniques to convey the weld characteristics. Audio cues may comprise playback of recorded audio and/or modulation of one or more of volume, pitch, tone, intensity, tempo, sound byte, sound sample, synthesized voice and/or tone and so forth. Audio cues may also include audio emission from a left or right audio source based on differences between preset weld parameters and detected weld parameters. In the illustrated embodiment, the audio component of the communication system 10 may be a temple transducer system, such as a bone conduction transducer, which may be mounted onto headgear around the temple of the user. Visual cues may include activation and/or manipulation of one or more lights (e.g., LEDs) or graphics that are arranged in positions correlative to particular aspects of weld characteristics being communicated, as will be discussed in detail below. For example, when the welding torch 16 is positioned too far to the right, lights arranged on a right side of the welding helmet 12 may be lit. In certain embodiments, the visual and/or audio components of the communication system 10 may be used to communicate system diagnostic information, such as battery level, wireless signal strength, and so forth, to the user.

In certain embodiments, the communication system 10 is configured to communicate a magnitude or degree of weld characteristics via audio and visual cues. For example, large errors committed by the welding operator 14 in positioning the welding torch 16 may be indicated by high intensity light and/or sound, while minor errors may be indicated by low intensity light and/or sound. Weld characteristic information may be obtained via sensors (e.g., a sensor that is integrated with the welding torch 16) and transmitted to the communication system 10 for processing. For example, the torch angle 22 may be measured with a sensor, such as an accelerometer, which detects the angle at which gravity pulls, and transmitted via a wireless link to the communication system 10. Additionally, in a constant voltage welding operation, the current emitted by the power source is generally a function of the tip-to-work distance 20 and thus may be used to determine the tip-to-work distance 20. Therefore, the tip-to-work distance 20 may be determined by measuring the current emitted at the primary power source with a sensor and processing that information via an algorithm in a processor within a sensor system. Subsequently, the tip-to-work distance 20 may be transmitted from the sensor system to the communication system 10 via a wireless or wired link. Once the communication system 10 receives data regarding the actual torch angle 22 and tip-to-work distance 20, additional algorithms may be executed by a processor in the communication system 10 that compare actual weld parameters to preset weld parameters. In other embodiments, a processor in the sensor system executes these additional algorithms that compare actual weld parameters to preset weld parameters. Discrepancies between actual weld parameters and preset weld parameters may then be transmitted to the user via video or audio cues that convey information to the welding operator 14. For example, one or more lights may be lit in the direction of the torch angle 22 error to indicate to the user that the torch 16 should be moved away from the direction of the lit lights.

Figure 2:
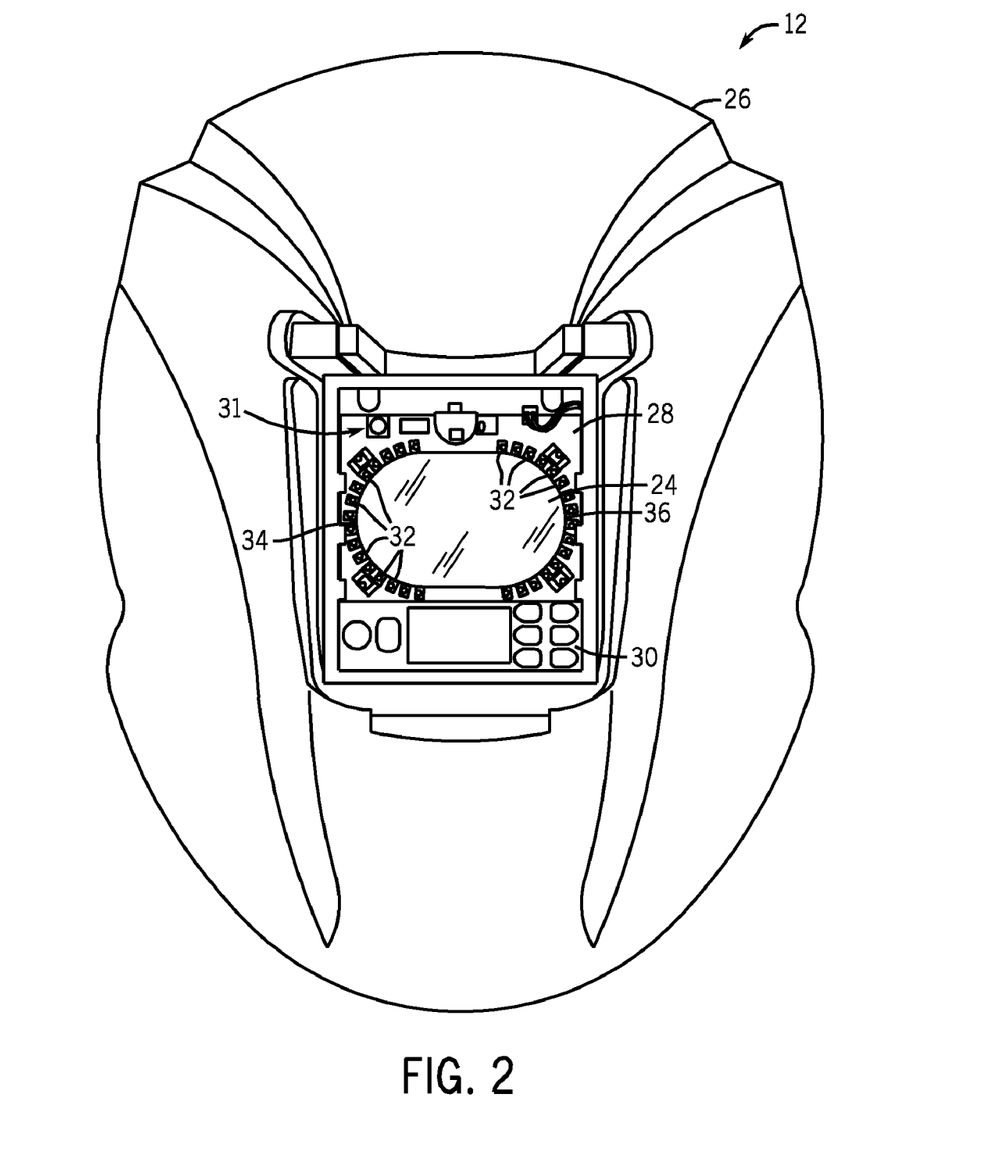
FIG. 2 illustrates one embodiment of the present disclosure in which a communication system is embedded in a welding helmet in accordance with aspects of the present disclosure.

FIG. 2 illustrates one embodiment of the present disclosure in which the communication system 10 is embedded in the welding helmet 12. A lens 24 is mounted to a shell 26 of the welding helmet 12. During use, the welding operator 14 views the welding operation through the lens 24, which may include a darkened or auto-darkening lens. In one embodiment, a weld information feedback (WIF) cartridge 28, a lens control system interface 30, and a WIF cartridge control interface 31 are mounted over the lens 24 on the side of the lens 24 facing the welding operator 14 during proper use of the welding helmet 12. As will be discussed below, the WIF cartridge 28 and the cartridge interface 31 may facilitate conveying information from the communication system 10 to the welding operator 14, and/or control of the communication system 10 by the welding operator 14. It should be noted that in other embodiments, the WIF cartridge 28, the cartridge interface 31, and/or certain components of each may be mounted in other locations, such as different locations in or on the welding helmet 12. For example, certain components of the cartridge interface 31 (e.g., a reset button) may be positioned on an outer portion of the welding helmet 12 to facilitate access during use of the helmet 12.

In the illustrated embodiment, the WIF cartridge 28 includes features that facilitate communication of weld characteristics to the welding operator 14 in substantially real time during a weld. Indeed, in the illustrated embodiment, the WIF cartridge 28 includes a visual component of the communication system 10. Specifically, in the embodiment shown, the WIF cartridge 28 includes an integrated series of visual indicators 32 arranged in two semicircles 34, 36 around the periphery of the lens 24. The visual indicators 32 in the illustrated embodiment are LEDs, but in other embodiments, the visual indicators 32 may be any combination of suitable switchable devices that are electrical, mechanical, or electromechanical, which emit light, allow light to pass through them, or reflect light. In one embodiment, the visual indicators 32 may all be provided in a single color. For example, all of the indicators 32 may be red LEDs to accommodate color blind users, and various light intensities may be utilized to convey additional information. In another embodiment, LEDs may be provided in multiple colors to facilitate communication of multiple weld characteristics. For example, LEDs of a certain color (e.g., red LEDs) may be utilized when the torch 16 is too close to the workpiece 18, and LEDs of another color (e.g., green LEDs) may be utilized when the torch 16 is too far away from the workpiece 18. In the illustrated embodiment, a single visual indicator 32 is positioned within each of a number of distinct positions along the internal edges of the WIF cartridge 28. However, in other embodiments, a cluster of two or more visual indicators 32 may be positioned in each distinct position to maintain redundancy or, specifically, the ability of the system to communicate with the welding operator 14 even if one of the visual indicators 32 is not functioning properly.

Figure 3:
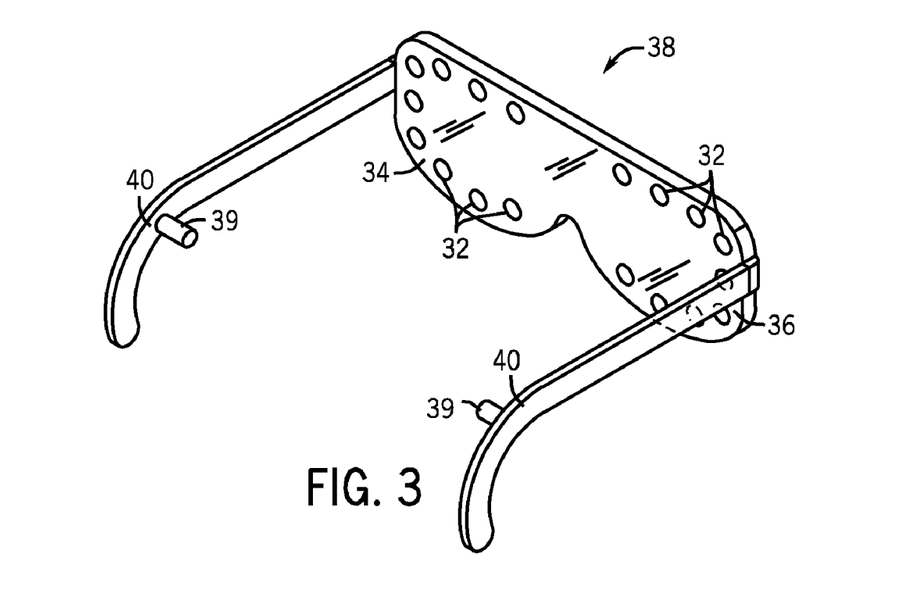
FIG. 3 illustrates one embodiment of the present disclosure in which a communication system is embedded in safety goggles or glasses in accordance with aspects of the present disclosure.

In some embodiments, the system 10 may not be fully integrated with the welding helmet 12. Indeed, the system may not be integrated with the welding helmet 12 at all, and/or the system 10 may be partially integrated with various different devices (e.g., a belt pack or goggles). For example, FIG. 3 illustrates one embodiment of the present disclosure in which components of the communication system 10 are embedded in safety glasses 38. The visual part of the communication system 10 in the illustrated embodiment of FIG. 3 is a series of visual indicators 32 arranged in two semicircles 34, 36 around the peripheries of the glasses 38. In this embodiment, the audio system may be a temple transducer system 39 mounted on securement bars 40 of the glasses 38. Additionally, the audio system may include headphones that fit in the ears of the user for audio communication. Such a system may allow the user to choose the volume, frequency, tone and so forth of the audio cues to ensure that the audio cues are distinguishable from sounds in the environment of the user.

Figure 4:
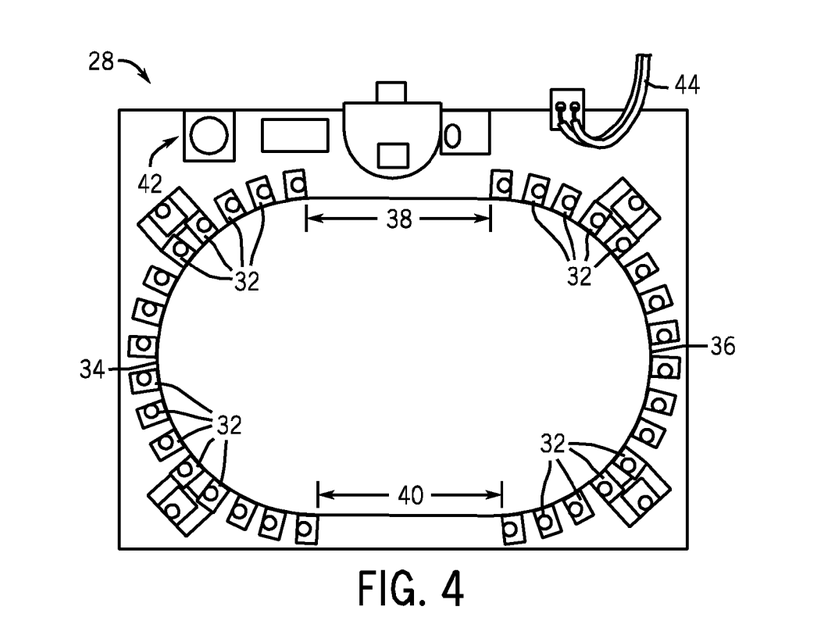
FIG. 4 illustrates an exemplary weld information feedback cartridge that informs a welding operator of welding torch angle information in real time during a welding operation in accordance with aspects of the present disclosure.

FIG. 4 illustrates the WIF cartridge 28 including a pair of arrays 34, 36 of the visual indicators 32, which may cooperate to inform the welding operator 14 of welding torch angle 22 and tip-to-work distance 20 information in real time during a welding operation. The WIF cartridge 28 may be utilized by the welding operator 14 to confirm that the welding operator 14 is holding the torch 16 within a correct range of angles relative to the workpiece 18 and within a correct range of distances from the workpiece 18 during the welding operation. The WIF cartridge 28 in the illustrated embodiment uses two semicircular arrays 34, 36 of sixteen LEDs 32 to communicate torch angle 22 information to the welding operator 14. The arrays of LEDs 34, 36 are separated by a gap 38 between the tops of the two semicircles 34, 36 and a gap 40 between the bottoms of the two semicircles 34, 36. The semicircles 34, 36 are arranged such that during operation they may appear to the welding operator 14 to be arranged in a continuous circle due to the close proximity of the WIF cartridge 28 to the face of the welding operator 14.

In one embodiment, a preset number of adjacent LEDs 32 or other visual indicators in the proper positions in the two semicircles 34, 36 may be lit to show the actual direction of the weld angle. This may intuitively indicate to the welding operator 14 that the torch 16 should be moved in the direction opposite the lit LEDs. For example, if the welding operator 14 moves the torch 16 too far to the right, four LEDs may light up on the right side of the WIF cartridge 28. The welding operator 14 may then move the torch 16 to the left to compensate for the error. Similarly, if the welding operator 14 moves the torch 16 too far to the left, four LEDs may light up on the left side of the WIF cartridge 28. The welding operator 14 may then move the torch 16 to the right to compensate for the error. An on/off state of each visual indicator may be individually controlled such that any combination of LEDs may be lit at a given time based on feedback from angle and/or distance sensors or the like. Additionally, the communication system 10 may be configured to track the progress of the welding operator 14. For instance, the system 10 may keep track of the number of welds performed, the number of errors per weld and so forth. An algorithm that assigns the welding operator 14 a performance score may be executed by the processor in the weld communication system 10. Such an algorithm may allow comparison between welding operators and may provide a quantitative indicator of welding operator experience and accuracy. The visual and/or audio components of the communication system 10 may be used to communicate such weld tracking information to the welding operator 14. Additionally, in certain embodiments, the brightness of the lit LEDs may correlate with the magnitude of the weld angle error. For instance, the brightness of the lit LEDs could increase as the angle of error increases. The communication system 10 may be configured to display discrete levels of brightness ranging from off to maximum brightness depending on how many degrees the torch angle is out of the preset range (i.e. for an angle error greater than 2 degrees, brightness level 1 is displayed while for an angle error greater than 4 degrees, brightness level 2 is displayed, and so forth). Similarly, the audio characteristics of the audio system (e.g. volume, frequency, pattern, and so forth) may correlate with the magnitude of tip-to-work distance 20 error. Cartridge control and support circuitry 42 may be mounted on the WIF cartridge 28, and a cable 44 may interface the WIF cartridge 28 with other communication system 10 components.

Figure 5:
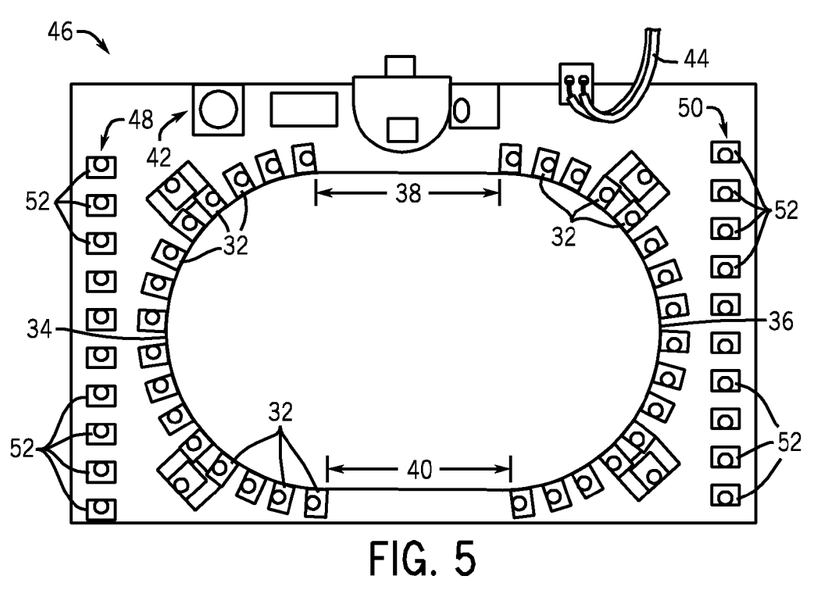
FIG. 5 illustrates an exemplary weld information feedback cartridge with two semicircles and two vertical arrays of visual indicators in accordance with aspects of the present disclosure.

FIG. 5 illustrates an exemplary WIF cartridge 46, which is similar to the exemplary WIF cartridge 28 illustrated in FIG. 4. In this embodiment, in addition to the two semicircles 34, 36 of visual indicators 32 that are configured to communicate torch angle 22 to the welding operator 14, two vertical arrays 48, 50 of visual indicators may be added on either side of the semicircular arrays 34, 36. The vertical arrays 48, 50 may be used to communicate weld characteristics such as control pedal position, torch travel speed and so forth. The visual indicators 52 of the vertical arrays 48, 50 may communicate information via visual cues such as color, brightness, intensity, position of lit indicators, number of lit indicators, blinking, frequency of blinking and so forth. For instance, the vertical visual indicators 52 may communicate torch travel speed via a bar graph method. Specifically, for example, a maximum speed may be indicated by activating all of indicators 52 of the vertical array 50, a minimum speed may be indicated by activating a single indicator 52 at a far end of the vertical array 50, and intermediate speeds may be indicated by activating a proportional number of indicators 52 such that increasing speeds cause the indicators to be activated in a sequential pattern until the maximum is reached. In one embodiment, a predetermined target travel speed may be indicated by a brightly lit indicator 52 at the midpoint of one or both of the vertical arrays 48, 50. While the welding operator 14 adjusts the travel speed of the torch 16, one or both of the vertical arrays 48, 50 may dimly light visual indicators 52 to reflect the actual value of the travel speed in a manner similar to a bar graph. For example, when the torch 16 travel speed exceeds the predetermined target level, indicators 52 above the brightly lit indicator 52 would dimly light up.

Similarly, when the torch 16 travel speed is slower than the predetermined target level, indicators 52 below the brightly lit indicator 52 would dimly light up. The goal of the user would be to keep only the brightly lit indicator 52 illuminated, which would indicate that the user was operating within the predetermined target level. In other embodiments, the goal of the user may be to have no indicators illuminated. Such a feature may be implemented for other weld characteristics (e.g. tip-to-work distance 20) as well.

Figure 6:
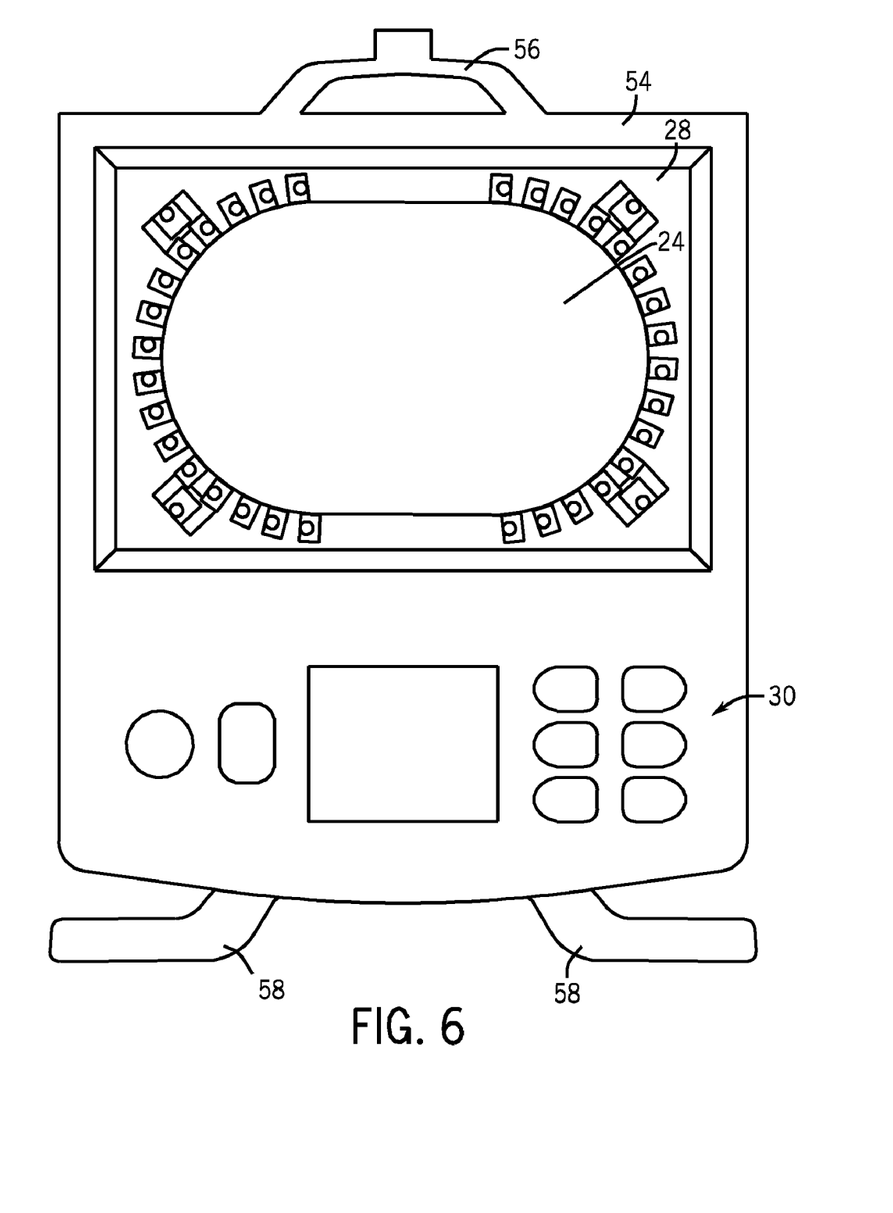
FIG. 6 illustrates one example of a position or placement of an exemplary weld information feedback cartridge behind a lens mounted on a lens cartridge and holder in accordance with aspects of the present disclosure.

Since the weld characteristic communication system 10 may be separate from the welding lens 24, existing welding helmets 12 may be easily upgraded to include the communication system 10. The communication system 10 may attach to the welding helmet 12 in a number of ways (i.e. clips, suction cups, adhesive, tape and so forth). FIG. 6 illustrates one way the WIF cartridge 28 may be integrated into existing welding helmets 12. In the embodiment illustrated in FIG. 6, the WIF cartridge 28 is positioned behind the lens 24 mounted on the lens cartridge holder 54, which is a removable piece that holds a welding lens 24 cartridge inside the welding helmet 12. In the embodiment shown, the lens cartridge holder 54 is configured to encase both the WIF cartridge 28 and the lens cartridge, which holds the lens 24. The lens cartridge holder 54 can be transferred between welding helmets 14, allowing the communication system 10 to be easily shared between users. In this embodiment, the system interface 30, which allows the user to control the operation of the welding lens 24, is positioned below the WIF cartridge 28. The lens cartridge and holder 54 may then be attached to the welding helmet 12 via appendices 56, 58 on the top and bottom of the holder 54. It should be noted that the WIF cartridge 28 (or any part of the communication system 10) may be integrated into a lens cartridge or any support structure provided for the lens 24 and its associated circuitry. Additionally, the WIF cartridge 28 may be inserted into a magnifying lens holder, which typically may be configured to hold a magnifying lens.

Figures 7, 9:
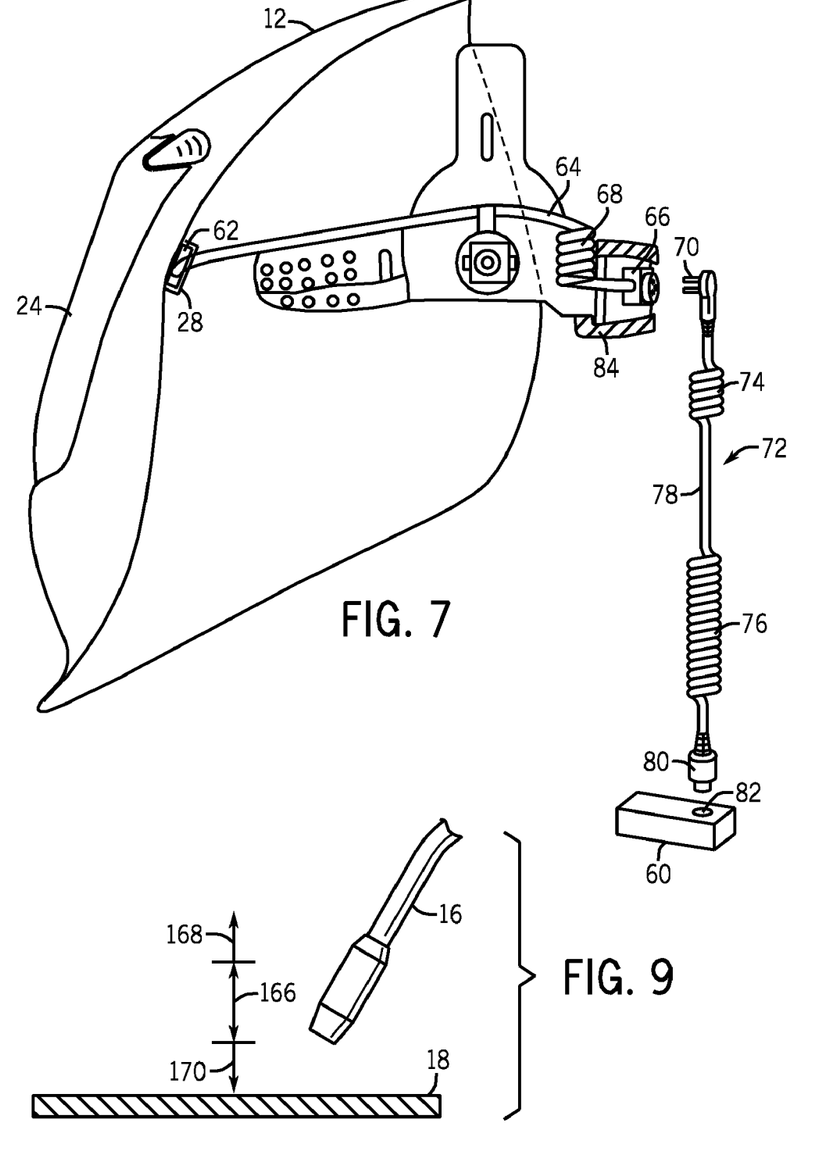
FIG. 7 illustrates an exemplary weld information feedback cartridge mounted behind a lens where some or all of the support and control circuitry is located in a belt pack in accordance with aspects of the present disclosure.
FIG. 9 illustrates a method of audio conveyance of the tip-to-work distance to a welding operator through a communication system in accordance with aspects of the present disclosure.

The communication system 10 utilizes support and control circuitry to power and control the physical operation of the system 10 and to process information transmitted from the sensor system. In one embodiment, all the support and control circuitry may be located in or on the welding helmet 12. FIG. 7 illustrates one embodiment of the present disclosure in which the WIF cartridge 28 is mounted behind the lens 24 in the welding helmet 12 and some of the support and control circuitry for the communication system 10 is not located in or on the welding helmet 12. In the illustrated embodiment, some or all of the support and control circuitry may be located in a belt pack 60, which may provide power for the communication system 10 and receive weld characteristic information from the sensor system, as previously discussed, which comprises sensors, software, and so forth. In one embodiment, a RS232 link may be used to communicate between the belt pack 60 and the WIF cartridge 28 or between the WIF cartridge 28 and the sensor system. In other embodiments, a wireless protocol, such as Bluetooth, may be used to communicate between the belt pack 60 and the sensor system. As previously mentioned, certain embodiments may eliminate the belt pack 60 and instead mount all the necessary components on the welding helmet 12. In the illustrated embodiment, a CONN1 socket and plug 62 connect a first coil cable 64 to a CONN2 socket 66. The CONN1 plug 62 may be a sub-micro connector, which is connected at a factory during installation. The CONN2 socket may be rated for at least 2000 or more mating cycles. A coil section 68 of the first cable 64 may expand to allow for helmet 12 movement. A CONN2 plug 70 may connect the helmet 12 to a second coil cable 72, which comprises an upper section 74 that expands to allow head movement, and a lower section 76, which expands to fit the body of the welding operator 14 and allows movement of the welding operator 14. A mid section 78 of the second cable 72 may comprise a device, such as a c-clip, which clips to the collar of the welding operator 14 and allows the second cable 72 to slide freely between the upper section 74 and the lower section 76 of the second cable 72. A CONN3 plug 80 connects the second cable 72 to the belt pack 60 via a CONN3 socket 82. A comfort cushion 84 may ensure comfort of the welding operator 14 during use. In certain embodiments, the first cable 64 and the second cable 72 may be lightweight, cut resistant, tear resistant, spark/heat resistant, and/or electrically shielded. In other embodiments, different configurations and connections types may be utilized.

Figure 8A:
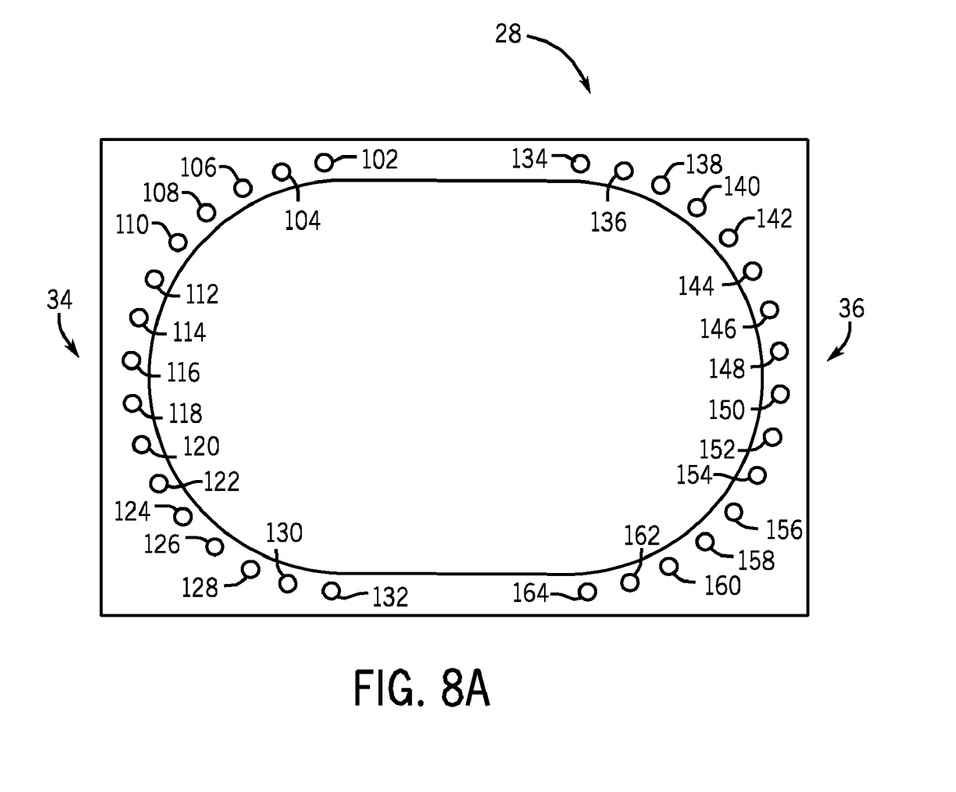
FIGS. 8A and 8B illustrates a method of visually conveying torch angle information to a welding operator through a communication system in accordance with aspects of the present disclosure.
Figure 8B:
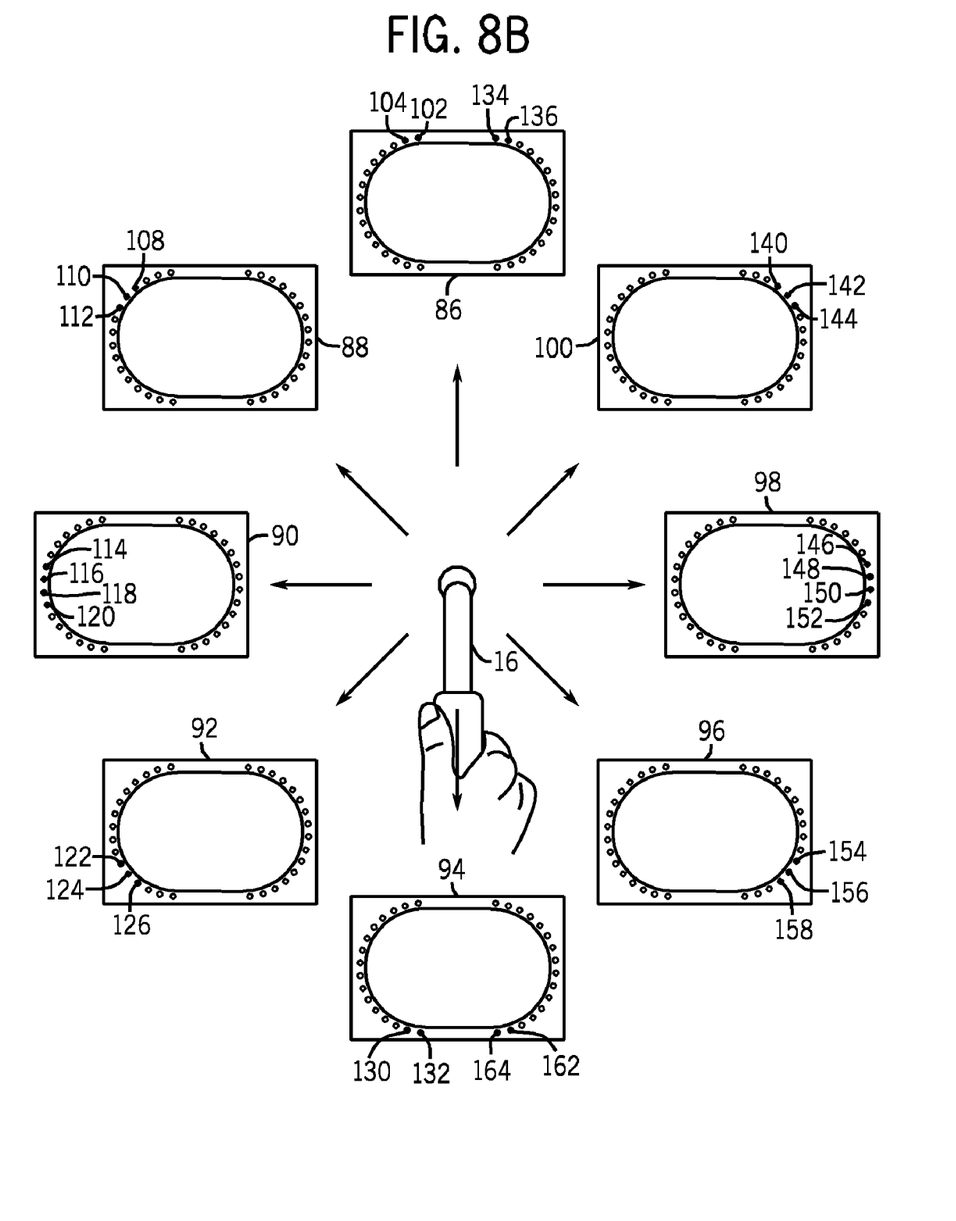

FIGS. 8A and 8B illustrate a method of visually conveying a torch angle 22 vector, which conveys both a magnitude and direction, to the welding operator 14 through the communication system 10 in accordance with aspects of the present disclosure. FIG. 8A includes a detailed view of the WIF cartridge 28. FIG. 8B illustrates eight possible exemplary configurations 86, 88, 90, 92, 94, 96, 98, 100 of lit visual indicators of the WIF cartridge 28 for explanatory purposes. However, one skilled in the art would understand that many more intermediate configurations may also be used. FIG. 8A illustrates an exemplary arrangement of visual indicators about a viewing area of a welding mask in accordance with present embodiments. Specifically, FIG. 8A illustrates the WIF cartridge 28 including an arrangement of visual indicators positioned about the lens 24 of the welding helmet 12, wherein each of the visual indicators is indicated by a reference number to facilitate explanation of modes of operation in accordance with present embodiments. The arrangement of LEDs includes a pair of semi-circular arrays 34 and 36 with LEDs 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162 and 164.

The semicircular arrays of visual indicators 34, 36 in FIG. 8A and FIG. 8B each comprise sixteen LEDs for explanatory purposes. However, one skilled in the art would understand that any number of LEDs could be used and that the visual indicators may not be LEDs. The shaded circles in FIG. 8B indicate lit LEDs while the unshaded circles indicate unlit LEDs. The arrows indicate which way the torch 16 was moved by the welding operator 14. Consider, for instance, the LED arrangement illustrated in configuration 98 in FIG. 8B. The four LEDs 146, 148, 150, 152 on the right side of the lens 24 are illuminated. Since the LEDs are activated to indicate when and in which direction the torch angle 22 is in error, this configuration 98 would indicate to the welding operator 14 that the torch angle 22 needs to be corrected by tilting the torch 16 toward the left side of the welding operator 14. Similarly, when the four LEDs 114, 116, 118, 120 on the left side of the lens 24 are illuminated, this configuration 90 would indicate to the welding operator 14 that the torch angle 22 needs to be corrected by tilting the torch 16 toward the right side of the welding operator 14. When the four LEDs 102, 104, 134, 136 on the top of the lens 24 are illuminated, this configuration 86 would indicate to the welding operator 14 that the torch angle 22 needs to be corrected by tilting the torch 16 toward the welding operator 14. Similarly, when the four LEDs 130, 132, 164, 162 on the bottom of the lens 24 are illuminated, this configuration 94 would indicate to the welding operator 14 that the torch angle 22 needs to be corrected by tilting the torch 16 back, away from the welding operator 14.

The intermediate configurations 88, 92, 96, 100 may communicate similar information to the user. For instance, consider the LED arrangement illustrated in configuration 88. The three LEDs 108, 110, 112 on the upper left side of the lens 24 are illuminated. Since the LEDs light to indicate when and in which direction the torch angle 22 is in error, this configuration 88 would indicate to the welding operator 14 that the torch angle 22 needs to be corrected by tilting the torch 16 toward the welding operator 14 and to the right. Similarly, when the three LEDs 126, 124, 122 on the bottom left side of the lens 24 are illuminated, this configuration 92 would indicate to the welding operator 14 that the torch angle 22 needs to be corrected by tilting the torch 16 away from the welding operator 14 and to the right. When the three LEDs 158, 156, 154 on the bottom right of the lens 24 are illuminated, this configuration 96 would indicate to the welding operator 14 that the torch angle 22 needs to be corrected by tilting the torch 16 away from the welding operator 14 and to the left. When the three LEDs 140, 142, 144 on the top right of the lens 24 are illuminated, this configuration 100 would indicate to the welding operator 14 that the torch angle 22 needs to be corrected by tilting the torch 16 toward the welding operator 14 and to the left. It should be noted that in other embodiments the LEDs may be used to indicate to the welding operator 14 which direction to move the torch 16 in a fashion opposite to the described method. For instance, the LEDs may be activated in the direction the welding operator 14 should move the torch 16 to maintain a proper torch angle 22 and not in the direction of torch angle 22 error. The welding operator 14 may then move the torch 16 toward the activated LEDs instead of away from the activated LEDs.

In total, there are eight configurations 86, 88, 90, 92, 94, 96, 98 and 100 of illuminated LEDs in the illustrated embodiment. Each configuration would indicate a 45 degree angle range of torch angle 22 correction. In certain embodiments, the brightness of the LEDs may be configured to increase as the angle of error increases. In other embodiments, the number of lit LEDs may be increased as the angle of error increases. Each visual indicator in the illustrated embodiment may be replaced with multiple indicators that light up to indicate the same position to prevent miscommunication when a single LED is not functioning or light up sequentially to indicate a degree of error. In other embodiments, a single LED instead of three or four may be used to indicate torch angle error. Each configuration may indicate 1 or more degrees of angle range of torch angle 22 correction (i.e. 360 configurations may be used instead of 8). The LEDs may be different colors or the same color. For instance, the LEDs on one side may be one color and, the LEDs on the other side may be a different color. Additionally, the LEDs may change color instead of brightness to indicate that the angle of error has increased beyond a certain setpoint and has greatly varied from the preset range.

In one embodiment, the communication system 10 may include various modes of operation. For example, the communication system 10 may include a system test mode. In the system test mode, a user may check to ensure proper system functioning prior to beginning a welding operation. For instance, the communication system 10 may comprise a test mode button on the system interface 30 that the user may depress to activate the test mode. Subsequently, while the communication system 10 is in test mode, the user may vary the torch angle 22 to verify that the correct visual indicators 32 light. A similar process may be used to engage and check the audio component of the communication system 10. Similarly, the communication system 10 may include a training mode, which may be used by inexperienced welding operators to perfect mechanical movement to achieve the proper torch angle and/or torch-to-workpiece distance without welding and thereby wasting consumables. Additional embodiments may allow the user to use the torch angle and torch-to-workpiece distance from a previous weld as the set point for successive welds.

FIG. 9 illustrates a method of audio conveyance of the tip-to-work distance 20 to the welding operator 14 through the communication system 10 in accordance with aspects of the present disclosure. In the illustrated embodiment, two distinct tones may sound to indicate when the torch 16 is outside a preset range 166 of tip-to-work distances. When the torch 16 is moved to a position such that the tip-to-work distance 20 is above a preset range 166, as indicated by arrow 168, a pulsed tone may be generated for the welding operator 14. When the torch 16 is moved to a position such that the tip-to-work distance 20 is below a preset range 166, as indicated by arrow 170, a continuous tone may be generated for the welding operator 14. In other embodiments, two distinct frequencies or audio patterns may be used to indicate that the tip-to-work distance 20 is above or below a preset range 166. In other embodiments, visual indicators may be used for an indication of tip-to-work 20 distance (e.g. a bar graph).

Figure 10:
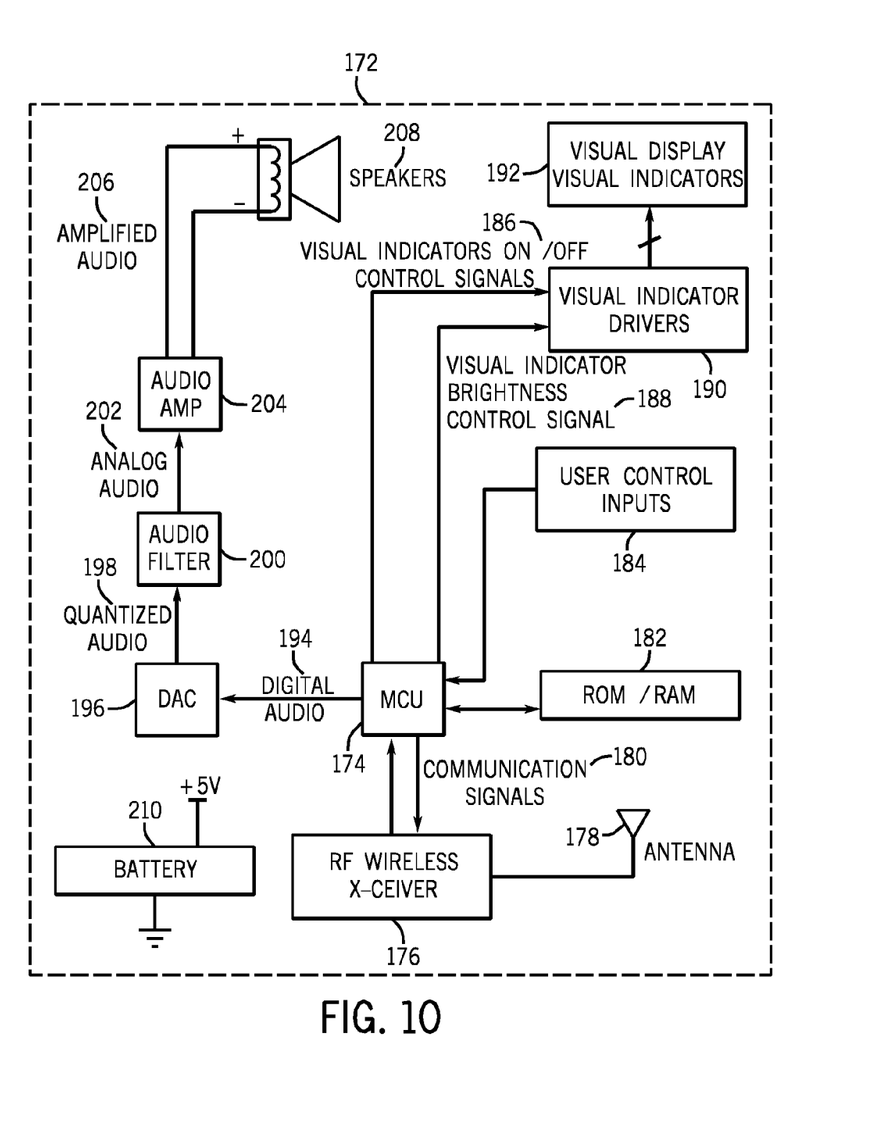
FIG. 10 illustrates an exemplary communication system diagram where all of the system components are mounted in or on a welding helmet, mask or the like in accordance with aspects of the present disclosure.

FIG. 10 is a system diagram illustrating exemplary components that may comprise the communication system 10. In the illustrated embodiment, all of the components would be mounted in or on the welding helmet as indicated by block 172. A microcontroller (i.e. MCU) 174 interfaces system components together, receiving and transmitting various control and processing signals. A wireless receiver 176 coupled to an antenna 178 communicates with the MCU 174 via two way communication signals 180. The wireless receiver 176 may receive information from the sensor system regarding sensed torch angle 22 and tip-to-work distance 20. The MCU 174 may then execute algorithms that process this information. The MCU 174 is communicatively coupled to a memory component (i.e. ROM/RAM) 182, through which the MCU 174 stores and retrieves information, such as the number of user errors, the number of user welds, the score of the user, and so forth. The MCU 174 receives user control inputs 184, such as audio volume, visual indicator brightness, power on/off, and so forth, which may be input via the system interface 30. The visual and/or audio components of the communication system 10 may be used to assist the user in adjusting system settings. For example, as the volume is changed, the audio component of the communication system 10 may emit a tone of the newly set volume, and the visual component of the communication system 10 may illuminate a series of visual indicators indicative of the newly set volume level. The user control inputs 184 may also be used to input the allowable ranges for angle and torch-to-workpiece distance. The MCU 174 outputs visual indicator on/off control signals 186 and visual indicator brightness control signals 188 that are received by visual indicator drivers 190 for each visual indicator in the communication system 10. For example, each of the visual indicators in FIG. 8 may be controlled by individual control signals 186, 188 so that the desired configuration of lit LEDs may be conveyed to the user. The visual drivers 190 implement the visual display 192 of the correct visual indicators. The MCU 174 also outputs a digital audio signal 194, which is received by a digital to analog converter (DAC) 196 and may convey weld characteristics, such as torch travel speed, tip-to-work distance 20 and so forth. The DAC 196 converts the digital signal 194 to a quantized audio signal 198, which is received by an audio filter 200. The audio filter 200 outputs an analog audio signal 202 that is received by an audio amplifier 204. The audio amplifier 204 outputs an amplified audio signal 206, which may be transmitted to the welding operator 14 via speakers 208. In other embodiments, the audio signal 206 may be transmitted to the user via audio systems other than speakers 208, such as bone conduction transducers. A battery 210 powers the communication system 10 in the helmet 172.

Figure 11:
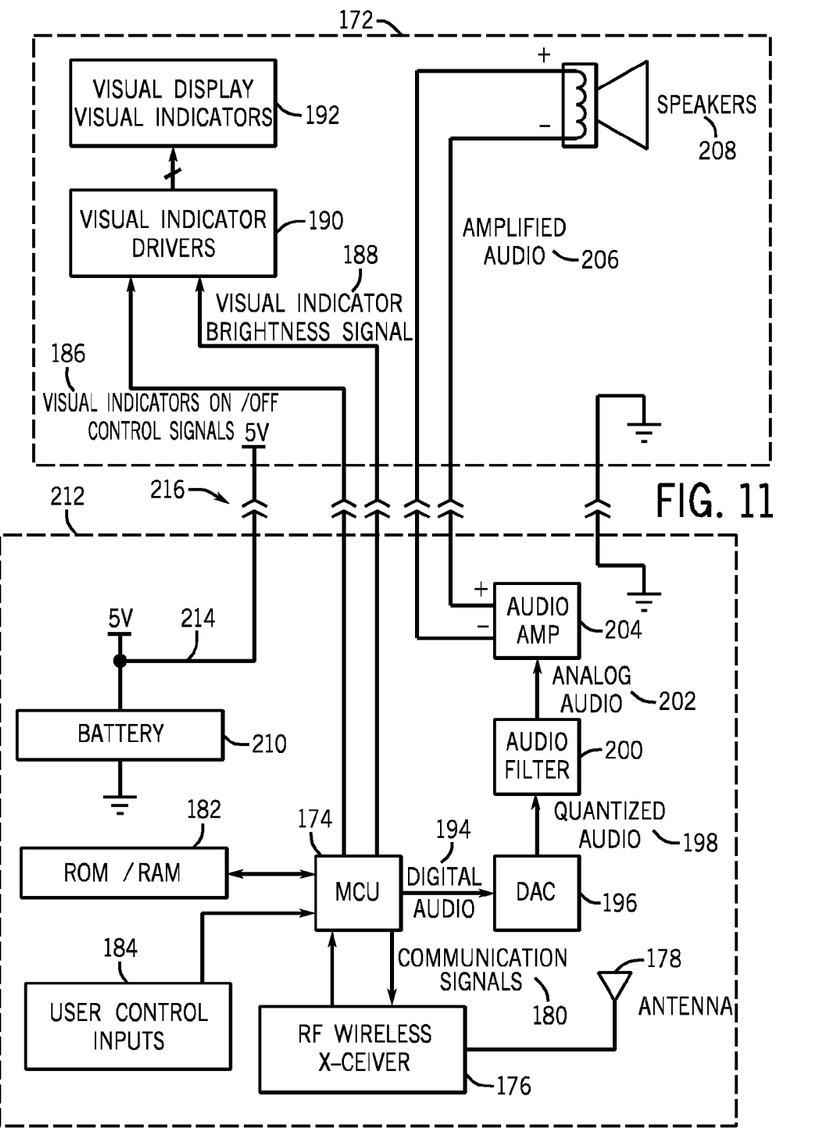
FIG. 11 illustrates an exemplary communication system diagram where the system components are mounted in a pack, such as a belt pack, and/or in a welding mask, such as a welding helmet, in accordance with aspects of the present disclosure.

FIG. 11 is a system diagram illustrating exemplary components that may comprise the communication system 10; the exemplary components may be communicatively coupled in the same way as previously described with respect to similar components in FIG. 10. However, in system diagram of FIG. 11, some of the components described in FIG. 10 may be mounted in or on the welding helmet 172, while the remaining components may be located in a belt pack 212. In other embodiments, the remaining components may be located in other locations on or around the welding operator 14 such as on the back of the headgear, on the jacket of the welding operator 14, and so forth. The visual indicator drivers 190, the visual display of the visual indicators 192, and the speakers would still be located in the helmet 172 as previously shown in FIG. 10. However, the MCU 174, the memory components 182, the battery 210, the user control inputs, 184, the wireless receiver 176, the antenna 178, the DAC 196, the audio filter 200 and the audio amplifier 204 are located in the belt pack 212. Additionally, a battery output 214, visual indicator brightness signals 188, visual indicator on/off signals 186 and amplified audio signals 206 are transmitted to components in the helmet 172 via a connector cable 216.

While only certain features of the present disclosure have been illustrated and described herein, many modifications and changes will occur to those skilled in the art. It is, therefore, to be understood that the appended claims are intended to cover all such modifications and changes as fall within the true spirit of the present disclosure.

The invention claimed is:

1. A welding helmet, comprising:
an audio device disposed in or on the welding helmet and configured to generate audio signals at a plurality of different pitches having a continuous or pulsed tone; and
a communication system configured to receive information regarding an error in a detected tip-to-work distance and to activate the audio device to generate an audio signal having a pitch and/or a tone that corresponds to the error in the detected tip-to-work distance.

2. The welding helmet of claim 1, wherein the communication system is configured to increase the pitch of the audio signal as the error in the received detected tip-to-work distance increases and to decrease the pitch of the audio signal as the error in the received detected tip-to-work distance decreases.

3. The welding helmet of claim 1, wherein when the detected tip-to-work distance is below a tip-to-work distance threshold, the communication system is configured to activate the audio device to generate the audio signal having a continuous tone.

4. The welding helmet of claim 1, wherein the communication system is configured to receive information regarding an error in a detected torch angle vector and to activate the audio device to generate a second audio signal having a pitch and/or a tone that corresponds to the error in the detected torch angle vector.

5. The welding helmet of claim 1, wherein the communication system is configured to receive information regarding an error in a detected travel speed and to activate the audio device to generate a second audio signal having a pitch and/or a tone that corresponds to the error in the detected travel speed.

6. The welding helmet of claim 1, wherein when the detected tip-to-work distance is above a tip-to-work distance threshold, the communication system is configured to activate the audio device to generate the audio signal having a pulsed tone.

7. The welding helmet of claim 1, wherein the audio device comprises a first audio source disposed in a first side of the welding helmet and a second audio source disposed in a second side of the welding helmet opposite the first side.

8. The welding helmet of claim 1, comprising a sensor disposed on a welding cable of a welding torch and being configured to detect the tip-to-work distance of the welding torch and to communicate the detected tip-to-work distance to the communication system.

9. A method of supplying welding information, comprising:
receiving data regarding a detected tip-to-work distance of a welding torch relative to a workpiece in a receiver;
determining, in a microcontroller, whether the detected tip-to-work distance is within a preset tip-to-work distance range;
determining, in a microcontroller, an error between the detected tip-to-work distance and a preset upper limit or a preset lower limit when the detected tip-to-work distance is not within the preset tip-to-work distance range; and
activating an audio device disposed in a welding mask to generate an audio signal having a pitch that varies in correspondence with the determined error.

10. The method of claim 9, comprising activating the audio device to generate the audio signal having a tone that corresponds to the direction of the error.

11. The method of claim 10, comprising activating the audio device to generate the audio signal having a pulsed tone when the direction of the error is above the preset upper limit.

12. The method of claim 9, wherein activating an audio device to generate the audio signal comprises generating the audio signal having a pitch that varies linearly with the determined error.

13. The method of claim 9, comprising receiving data regarding a detected travel speed and/or a detected torch angle vector of a welding torch and determining whether the received travel speed and/or the received torch angle vector exceeds a respective threshold.

14. The method of claim 13, comprising activating the audio device disposed in the welding mask to generate a second audio signal having a pitch and/or a tone that varies in correspondence with the determined error in the travel speed and/or the torch angel vector.

15. A welding mask, comprising:
a viewing area;
an audio device configured to generate an audio signal at a plurality of different pitches having a continuous or pulsed tone; and
a communication system configured to receive information regarding error values for positioning of a torch relative to a workpiece, wherein the error values include at least one of an error in a detected tip-to-work distance relative to a first preset value, an error in a detected torch angle vector relative to a second preset value, and/or an error in a detected travel speed relative to a third preset value, wherein the communication system is configured to activate the audio device to generate the audio signal with a selected pitch and a continuous or pulsed tone each corresponding to the direction of the error values.

16. The welding mask of claim 15, wherein the first preset value is a lower limit of a predetermined acceptable tip-towork distance range, and the communication system is configured to activate the audio device to generate the audio signal at a continuous tone when the error in the detected tip-to-work distance is below the first preset value.

17. The welding mask of claim 15, wherein the first preset value is an upper limit of a predetermined acceptable tip-to-work distance range, and the communication system is configured to activate the audio device to generate the audio signal at a pulsed tone when the error in the detected tip-to-work distance is above the first preset value.

18. The welding mask of claim 15, comprising a sensor system having a first sensor configured to measure a tip-to-work distance of the welding torch, a second sensor configured to measure the torch angle of the welding torch, and a third sensor configured to measure the travel speed of the welding torch.

19. The welding mask of claim 18, wherein the sensor system is configured to communicate measurements made by the first sensor, the second sensor, and/or the third sensor to the communication system.

20. The welding mask of claim 15, wherein the audio device comprises a first audio source disposed in a first side of the welding mask and a second audio source disposed in a second side of the welding mask opposite the first side.

* * * * *